United States Patent [19]

Tantau

[11] Patent Number: Plant 5,706

[45] Date of Patent: Apr. 1, 1986

[54] ROSE PLANT-JP 614-TANSENFRI

[75] Inventor: Mathias Tantau, Uetersen, Fed. Rep. of Germany

[73] Assignee: Jackson & Perkins Company, Medford, Oreg.

[21] Appl. No.: 634,765

[22] Filed: Jul. 26, 1984

[51] Int. Cl.[4] ..... A01H 5/00

[52] U.S. Cl. ..... Plt./24

[58] Field of Search ..... Plt./24

*Primary Examiner*—Robert E. Bagwill

*Attorney, Agent, or Firm*—Klarquist, Sparkman, Campbell, Leigh & Whinston

[57] ABSTRACT

A floribunda rose variety having an upright plant, blooms borne either in clusters or one per stem, consistent yellow orange flower color, slight fragrance, strong foliage, flat open flower form, and good resistance to rose powdery mildew and rose blackspot disease.

1 Drawing Figure

This present invention relates to a new and distinct variety of rose plant of the floribunda class which was originated by me by crossing an unnamed variety with an unnamed variety.

The primary objective of this breeding was to produce a new rose variety of the floribunda class, bearing large blooms of a deep yellow color on an upright, relatively disease resistant plant.

This objective was substantially achieved along with other desirable improvements as evidenced by the following unique combination of characteristics which are outstanding in the new variety and which distinguish it from its parents as well as from all other varieties of which I am aware:

1. A vigorous, upright plant.
2. Blooms borne in clusters as well as one per stem.
3. Consistent flower color of yellow orange fading very little after three days.
4. Slight fragrance.
5. Good resistance to rose powdery mildew and rose blackspot diseases.
6. Strong leathery foliage.
7. Quite flat open flower form with some undulation of petal edges.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Unnamed variety.

Classification:

*Botanical.*—Rosa hybrid.

*Commercial.*—Floribunda.

FLOWER

Observations made from specimens grown at Irvine, Calif. in November.

Blooming habit: Continuous.

Bud:

*Size.*—1" to 1½" when petals start to unfurl.

*Form.*—Long, blunt top.

*Color.*—When sepals first divide, near Yellow-Orange 22A. When half blown, upper side of petals Yellow-Orange 21A; lower side of petals Yellow-Orange 21A.

*Sepals.*—Color: Green 138A. Surface texture: Nearly smooth with very little fine pubescence. Three appendaged sepals lightly appendaged. Two unappendaged sepals hairy edged.

*Receptacle.*—Color: Green 138A. Shape: Funnel. Size: Large. Surface: Nearly smooth, very slightly hairy.

*Peduncle.*—Length: Short. Surface: Smooth, occasionally prickly. Color: Light green. Strength: Stiff, erect, heavy.

Bloom:

*Size.*—Large. Average open size: 3½" to 4".

*Borne.*—Singly or in clusters (flat).

*Stems.*—Short, strong.

*Form.*—When first open, high centered. Permanence: Flattens, outer petal edges slightly undulated.

*Petalage.*—Number of petals under normal conditions 25–30.

*Color.*—Center of flower: Upper side of petals Yellow-Orange 21A; reverse side of petals Yellow-Orange 21A; base of petals Yellow-Orange 21A. Major color: Yellow-Orange 21A.

*Variegations.*—Occasional vegetative streaks in outer petals.

*Discoloration.*—General tonality at end of first day: No change. Third day: Slightly lighter to Yellow-Orange 21B or 21C.

*Fragrance.*—Slight.

Petals:

*Texture.*—Thick.

*Shape.*—Round.

*Form.*—Edges slightly undulated.

*Arrangement.*—Imbricated. Petaloids in center: Many.
*Persistence.*—Drop off cleanly.
*Lastingness.*—On the plant, long. As cut flower, long.

Reproductive parts:
*Anthers.*—Medium, many. Color: Yellow. Arrangement: Regular around styles.
*Filaments.*—Color: Yellow.
*Pollen.*—Gold yellow.
*Styles.*—Color: Greenish white.
*Stigmas.*—Color: Greenish white.

PLANT

Form: Bush.
Growth: Vigorous, upright.
Foliage: Number of leaflets on normal mid-stem leaves: usually 5.
*Size.*—Large.
*Quantity.*—Normal.
*Color.*—New foliage: Green overlaid with Greyed Purple 183B. Old foliage: Normal green, non-glossy surface.

Leaflets:
*Shape.*—Broadly oval.
*Texture.*—Leathery on upper side.
*Edge.*—Serrated.

*Serration.*—Single, large.
*Petiole.*—Rachis: Color: Reddish. Underside with prickles.
*Stipules.*—Long, bearded.
*Disease resistance.*—Resistant to mildew, blackspot under normal growing conditions at Irvine, Calif.

Wood:
*New wood.*—Color: Light green. Bark: Smooth.
*Old wood.*—Color: Green. Bark: Smooth.

Prickles:
*Quantity.*—On main canes from base: Many. On laterals from main canes: Many.
*Form.*—Long, straight.
*Color when young.*—Brown.

Small prickles:
*Quantity.*—On main stalks: Few. On laterals: Few.
*Color.*—Brown.

I claim:

1. A new and distinct variety of rose plant of the floribunda class, substantially as herein shown and described, characterized particularly as to novelty by the unique combination of its disease resistant, upright plant, bearing yellow-orange blooms in clusters and singly, blooms being approximately 4″ across and of slight fragrance.

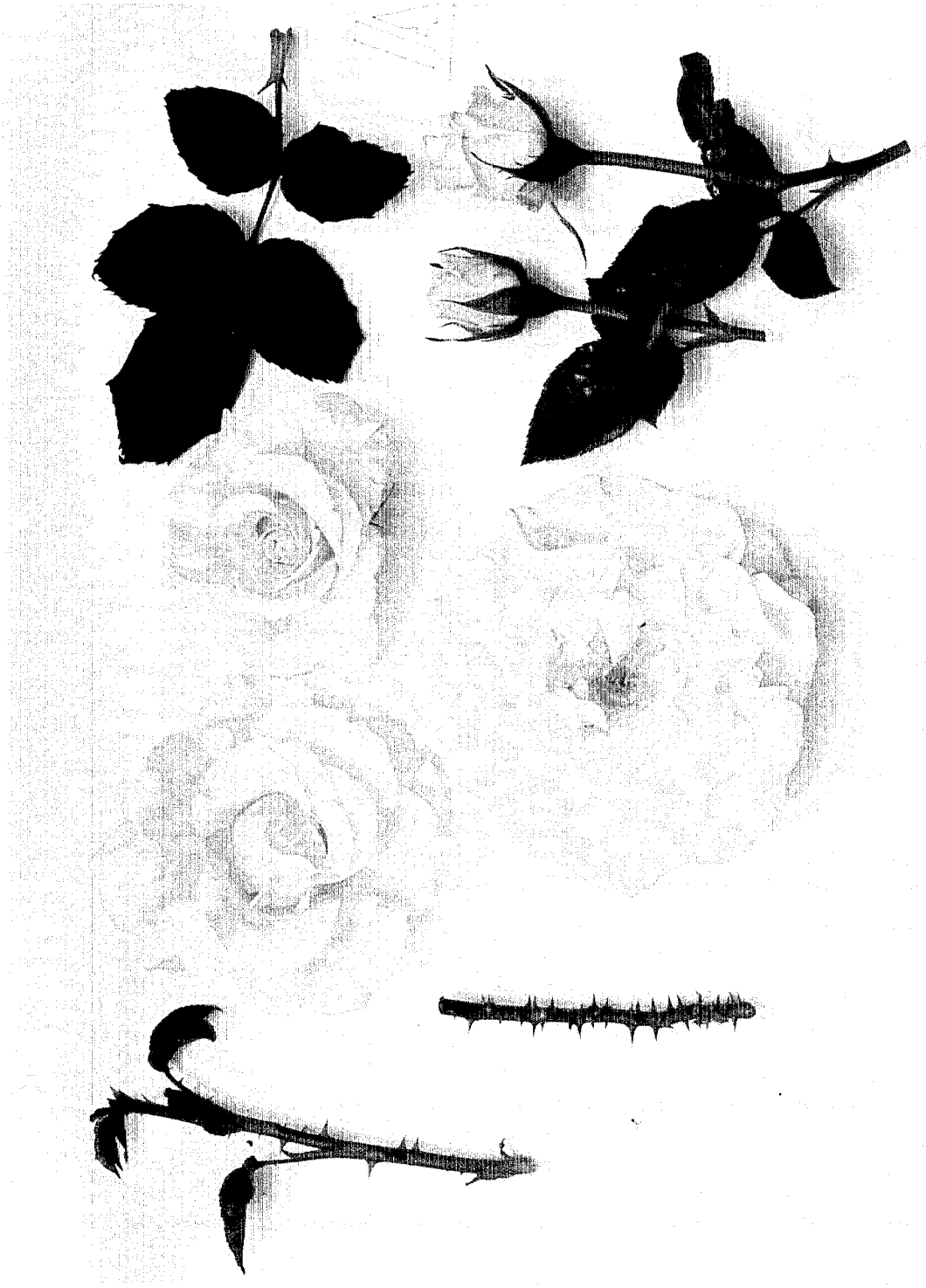

* * * * *